United States Patent
Ho (10) Patent No.: US 11,544,417 B2
(45) Date of Patent: Jan. 3, 2023

(54) METHOD OF GENERATING A CONFIGURATION FOR A CUSTOMIZED HEADGEAR

(71) Applicant: KONINKLIJKE PHILIPS N.V., Eindhoven (NL)

(72) Inventor: Peter Chi Fai Ho, Pittsburgh, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1040 days.

(21) Appl. No.: 16/307,693

(22) PCT Filed: Jun. 28, 2017

(86) PCT No.: PCT/EP2017/066049
§ 371 (c)(1),
(2) Date: Dec. 6, 2018

(87) PCT Pub. No.: WO2018/002169
PCT Pub. Date: Jan. 4, 2018

(65) Prior Publication Data
US 2019/0258749 A1    Aug. 22, 2019

Related U.S. Application Data

(60) Provisional application No. 62/355,982, filed on Jun. 29, 2016.

(51) Int. Cl.
*G06F 30/00* (2020.01)
*A61M 16/06* (2006.01)
(Continued)

(52) U.S. Cl.
CPC ......... *G06F 30/00* (2020.01); *A61M 16/0605* (2014.02); *A61M 16/0683* (2013.01);
(Continued)

(58) Field of Classification Search
CPC ........... A61M 16/06–0694; A61M 2016/0661; A61M 2207/00; A61M 2207/10;
(Continued)

(56) References Cited

U.S. PATENT DOCUMENTS 9,878,118 B2    1/2018  Formica
2006/0023228 A1  2/2006  Geng
(Continued)

FOREIGN PATENT DOCUMENTS

JP    2003301312 A    10/2003
WO   WO-2006130903 A1 * 12/2006 ............ A61M 16/06
(Continued)

*Primary Examiner* — Valerie L Woodward
(74) *Attorney, Agent, or Firm* — Michael W. Haas (57) ABSTRACT

A method of generating a customized headgear that includes a plurality of physical features and being usable with a mask component that supplies a flow of breathing gas to the patient's airways. The method includes receiving one or more parameters pertaining to the patient's head, subjecting at least some of the parameters to one or more algorithms to determine at least one of a length of a physical feature of the plurality of physical features and an angle between a pair of physical features of the plurality of physical features, generating an outline of at least a portion of a body which, when formed, is usable to assemble therefrom at least a portion of the headgear, and outputting a pattern usable to enable the formation of the at least portion of the body from at least a first sheet of at least a first material.

9 Claims, 7 Drawing Sheets

(51) Int. Cl.
*A62B 18/04* (2006.01)
*G06F 119/18* (2020.01)

(52) U.S. Cl.
CPC ....... *A61M 16/0694* (2014.02); *A62B 18/045* (2013.01); *A61M 2016/0661* (2013.01); *A61M 2207/00* (2013.01); *A61M 2207/10* (2013.01); *G06F 2119/18* (2020.01)

(58) Field of Classification Search
CPC ......... A62B 18/00–10; G06F 30/00–12; G06F 2119/18
See application file for complete search history.

(56) References Cited

U.S. PATENT DOCUMENTS

| | | | |
|---|---|---|---|
| 2009/0250065 A1* | 10/2009 | Omura | A61M 16/0683 128/207.11 |
| 2009/0266362 A1 | 10/2009 | Mark | |
| 2011/0197341 A1* | 8/2011 | Formica | B32B 27/065 2/209.3 |
| 2012/0305003 A1 | 12/2012 | Mark | |
| 2014/0209098 A1* | 7/2014 | Dunn | A61M 16/06 112/475.11 |
| 2014/0305439 A1 | 10/2014 | Chodkowski | |
| 2015/0217518 A1* | 8/2015 | Chun | A61M 16/06 700/98 |
| 2015/0217520 A1 | 8/2015 | Karpas et al. | |
| 2016/0143766 A1* | 5/2016 | Krishnasamy | A61M 16/0683 156/379.8 |
| 2019/0160247 A1* | 5/2019 | Kimmel | G06T 17/00 |
| 2019/0247604 A1 | 8/2019 | Dunn | |
| 2021/0008320 A1 | 1/2021 | Yu | |
| 2021/0085908 A1 | 3/2021 | Dunn | |
| 2022/0072256 A1 | 3/2022 | Amarasinghe | |

FOREIGN PATENT DOCUMENTS

| | | |
|---|---|---|
| WO | 2013026091 A1 | 2/2013 |
| WO | 2013026092 A1 | 2/2013 |
| WO | 2013064930 A1 | 5/2013 |
| WO | 2014165906 A1 | 10/2014 |
| WO | 2015043119 A1 | 4/2015 |
| WO | 2015043229 A1 | 4/2015 |
| WO | 2016000040 A1 | 1/2016 |
| WO | 2016085464 A1 | 6/2016 |

* cited by examiner

All Linear Dimensions in MM

| Input | Measurement | Design Nominal value (DNV) | Difference (Design-Measure) | | Remarks |
|---|---|---|---|---|---|
| UHC | 600 | 550 | -50 | | |
| LHC | 610 | 475 | -135 | | |
| E2E | 460 | 440 | -20 | | |
| D | 115 | 110 | -5 | | |
| Parameters | Nominal | Estimated Adjustment Value (EAV) | Output | | Remarks |
| A1 | 60.0 | | 60.0 | | Remain unchanged |
| A2 | 155.0 | -4.5 | 150.5 | | A2=180-A3 |
| A3 | 25.0 | 4.5 | 29.5 | | Calculated from adjusted A7 |
| A4 | 33.4 | 0.0 | 33.4 | | 0 |
| A5 | 101.9 | | 101.9 | | Remain unchanged |
| A6 | 102.0 | | 102.0 | | Remain unchanged |
| A7 | 42.5 | 2.3 | 44.8 | | A7=(A1+A3)/2=2*(ASIN(SQRT((((L3NOM + D + 142)/2 - L3NOM) * ((3NOM + D + 142)/2 - D)/L3NOM*D))) |
| L1 | 270 | 25 | 295 | | EAV=INT((UHC-DNV)/2) |
| L2 | 295 | 67 | 362 | | EAV=INT((LHC-DNV)/2) |
| L3 | 80 | 4.1 | 84 | | EAV=(E2E-DNV)/2*ATAN(A3) |
| L4 | 105 | 20 | 125 | | EAV=E2E-DNV |

METHOD OF GENERATING A CONFIGURATION FOR A CUSTOMIZED HEADGEAR

CROSS-REFERENCE TO RELATED APPLICATIONS

This application claims the priority benefit under 35 U.S.C. § 371 of International Patent Application No. PCT/EP2017/066049, filed on 28 Jun. 2017, which claims the priority benefit of U.S. Provisional Patent Application No. 62/355,982, filed on 29 Jun. 2016, the contents of which are herein incorporated by reference.

BACKGROUND OF THE INVENTION

1. Field of the Invention

The present invention relates to patient interface devices for transporting a gas to and/or from an airway of a patient and, in particular, to a method of generating a configuration for a headgear that is customized for a particular patient.

2. Description of the Related Art

Numerous situations exist wherein it is necessary or desirable to deliver a flow of breathing gas non-invasively to an airway of a patient, i.e., without intubating the patient or surgically inserting a tracheal tube in the esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion that rests beneath the patient's nose (such as a "pillows" style nasal cushion having nasal prongs that are received within the patient's nostrils or a "cradle" style nasal cushion that rests beneath and covers the patient's nostrils), a nasal/oral mask that covers the nose and mouth, or a full face mask that covers the patient's face. The patient interface device interfaces the ventilator or pressure support device with the airway of the patient so that a flow of breathing gas can be delivered from the pressure/flow generating device to the airway of the patient. It is known to maintain such devices on the face of a wearer by a headgear having one or more straps adapted to fit over/around the patient's head.

Due to the variability of shapes and sizes of the heads of patients, numerous types and configurations of headgear are available for selection by a professional to suit the needs of any given patient. However, most headgear is intended to be worn by a large number of people having different head shapes and sizes, and thus any given headgear typically is not necessarily customized for any particular patient and rather is intended to fit a variety of patents. While some success has been achieved in selecting pre-designed headgear for patients and achieving a reasonable fit with such patients, the fit is still, on the whole, at best only what can be reasonable achieved with a headgear that is intended for use with a range of head sizes and shapes, which is not an optimum fit. Improvements thus would be desirable.

SUMMARY OF THE INVENTION

Accordingly, it is an object of the present invention to provide a method of generating a configuration for a headgear that is customized for a particular patient and that overcomes the shortcomings of conventional methods. This object is achieved according to one embodiment of the present invention by providing an improved method of generating a configuration for a headgear that is customized for a particular patient who is in need of respiratory therapy, the headgear having a plurality of physical features and being usable with a mask component that supplies a flow of breathing gas to the patient's airways. The method can be generally stated as including receiving one or more parameters pertaining to the patient's head, subjecting at least some of the parameters to one or more algorithms to determine at least one of a length of a physical feature of the plurality of physical features and an angle between a pair of physical features of the plurality of physical features, generating an outline of at least a portion of a body which, when formed, is usable to assemble therefrom at least a portion of the headgear, the outline including the at least one of a length of a physical feature of the plurality of physical features and an angle between a pair of physical features of the plurality of physical features, and outputting a pattern that is visible and that comprises the outline, the pattern being usable to enable the formation of the at least portion of the body from at least a first sheet of at least a first material.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
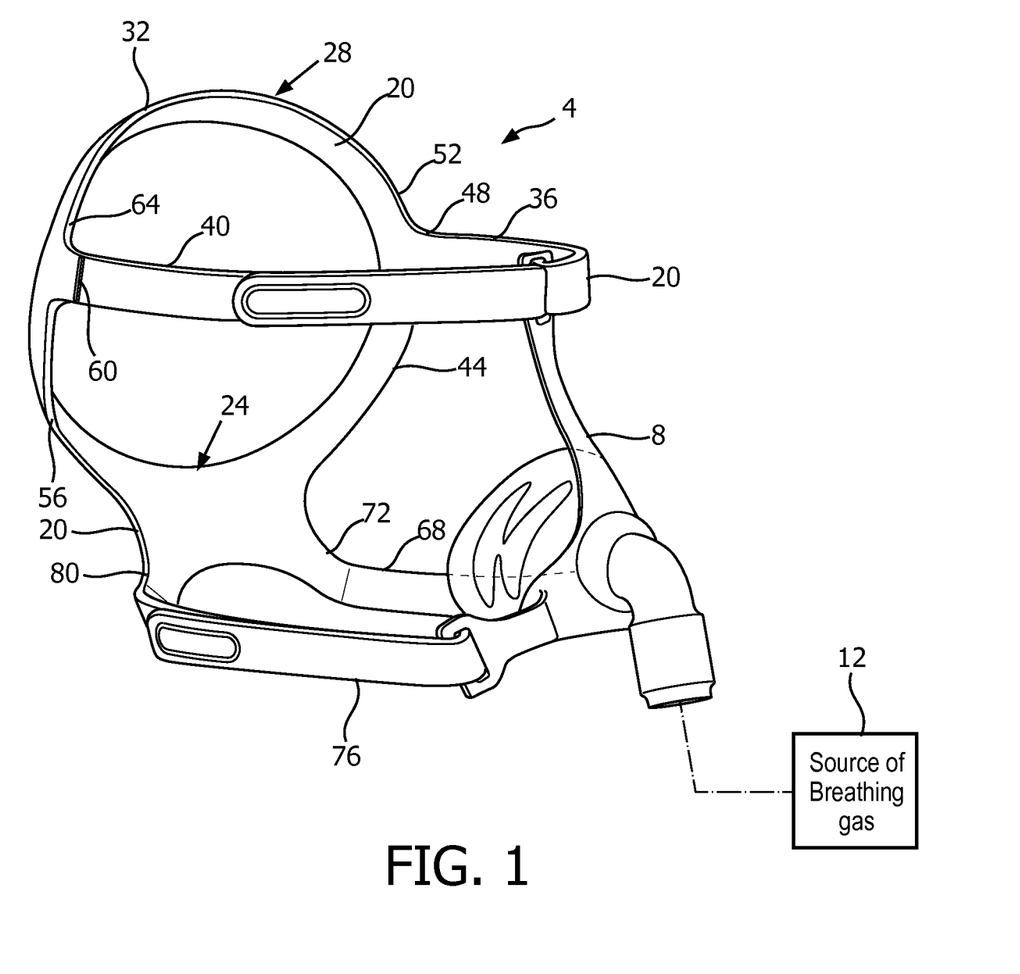
FIG. 1 is schematic depiction of a headgear connected to mask components and that is made according to principles of the present invention.

An improved headgear 4 that results from an improved method in accordance with the disclosed and claimed concept is depicted in FIG. 1. Headgear 4 is depicted as being connected with a mask component 8 that is connected in fluid communication with a supply of breathing gas 12. It is understood that the supply of breathing gas 12 provides a flow of breathing gas that is supplied via mask component 8 to a patient 16 (FIG. 2) who is in need of respiratory therapy. It is understood that mask component 8 is in fluid communication with the airways of patient 16 and that headgear 4 secures the mask components on patient 16. As will be set forth in greater detail below, headgear 4 is made in accordance with an improved method that is in accordance with the disclosed and claimed concept whereby headgear 4 is customized to suit the particular patient 16 in order to advantageously provide an improved fit.

Headgear 4 can be said to include a plurality of physical features 20 that can be said to comprise a base 24 and a strap apparatus 28 that extends from and is connected with base 24. Strap apparatus 28 can be said to include a parietal strap 32, a left temporal strap 36, and a right temporal strap 40. Strap apparatus 28 further includes a left occipital strap 44 having a left temporal attachment point 48 and a left parietal attachment point 52. Further, strap apparatus 28 includes a right occipital strap 56 having a right temporal attachment point 60 and a right parietal attachment point 64. Additionally, strap apparatus 28 includes a left chin strap 68 that is connected with a left chin attachment point 72 and further includes a right chin strap 76 that is connected with a right chin attachment point 80. It can be understood that parietal strap 32 extends across the parietal region of patient 16, that left and right temporal straps 36 and 40 extend across the temporal region of patient 16, and that left and right occipital straps 44 and 56 extend across the occipital region of patient 16 when headgear 4 is installed on patient 16. Likewise, left and right chin straps 68 and 76 extend between base 24 and the chin region of patient 16 when headgear 4 is installed on patient 16.

Figure 2:
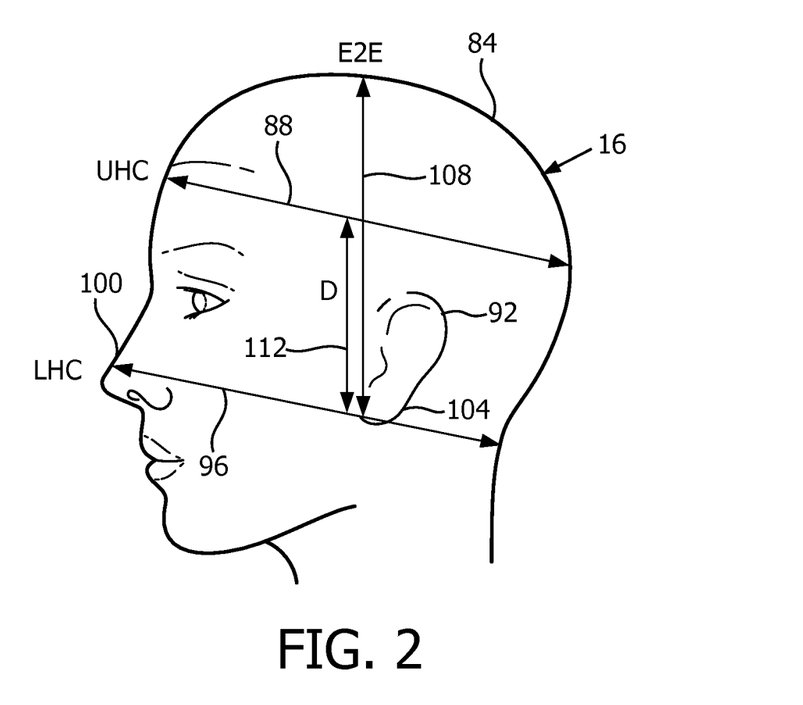
FIG. 2 is a schematic depiction of a patient who is in need of respiratory therapy.

Patient 16 has a head 84 and a pair of ears 92 that include a pair of earlobes such as depicted generally in FIG. 2, and head 84 has a size and shape that is specific to patient 16. An improved method that is in accordance with the disclosed and claimed concept and that will be described in greater detail below involves receiving from patient 16 a number of parameters that pertain to head 84. Specifically, the parameters include an upper head circumference (UHC) 88 that is measured around the head circumference between the forehead and the parietal region, and which is measured above ears 92. The parameters further include a lower head circumference (LHC) that is measured between the tip of the nose 100 and the occipital region, and which is measured below earlobes 104. The parameters further include an earlobe to earlobe length (E2E) 108 measured between earlobes 104 across the crown of head 84. Additionally, the parameters include a distance (D) 112 that is measured between upper head circumference 88 and lower head circumference 96. These four aforementioned parameters are merely exemplary in nature, and is understood that additional parameters or different parameters or both can be employed in developing the advantageous configuration for headgear 4.

It is envisioned that patient 16 can himself or herself measure the parameters of head 84, although the parameters can be measured by a healthcare professional or other individual. This measurement can be made using any suitable technique or measuring device. The parameters, once measured, are then input into a computer 116, such as is depicted in a schematic fashion in FIG. 4. Computer 116 is a general purpose computer, although it could be purpose built without departing from the present concept. Computer 116 can be said to include a processor apparatus 120, an input apparatus 124 that provides input signals to processor apparatus 120, and an output apparatus 128 that receives output signals from processor apparatus 120. Processor apparatus 120 can be said to include a processor 132 and to further include a storage 136 having one or more routines 140 stored therein. Processor 132 can be any of a wide variety of processors, including microprocessors, and the like. Storage 136 can be any of a wide variety of storage systems and can include RAM, ROM, EPROM, FLASH, and the like without limitation. Routines 140 are in the form of instructions that are stored in storage 136 and that are executable by processor 132 to cause computer 116 to perform various operations such as are set forth herein. It is expressly noted that computer 116 could be, in whole or in part, cloud-based and is not limited to physical hardware that is situated at any given physical location.

Figure 4:
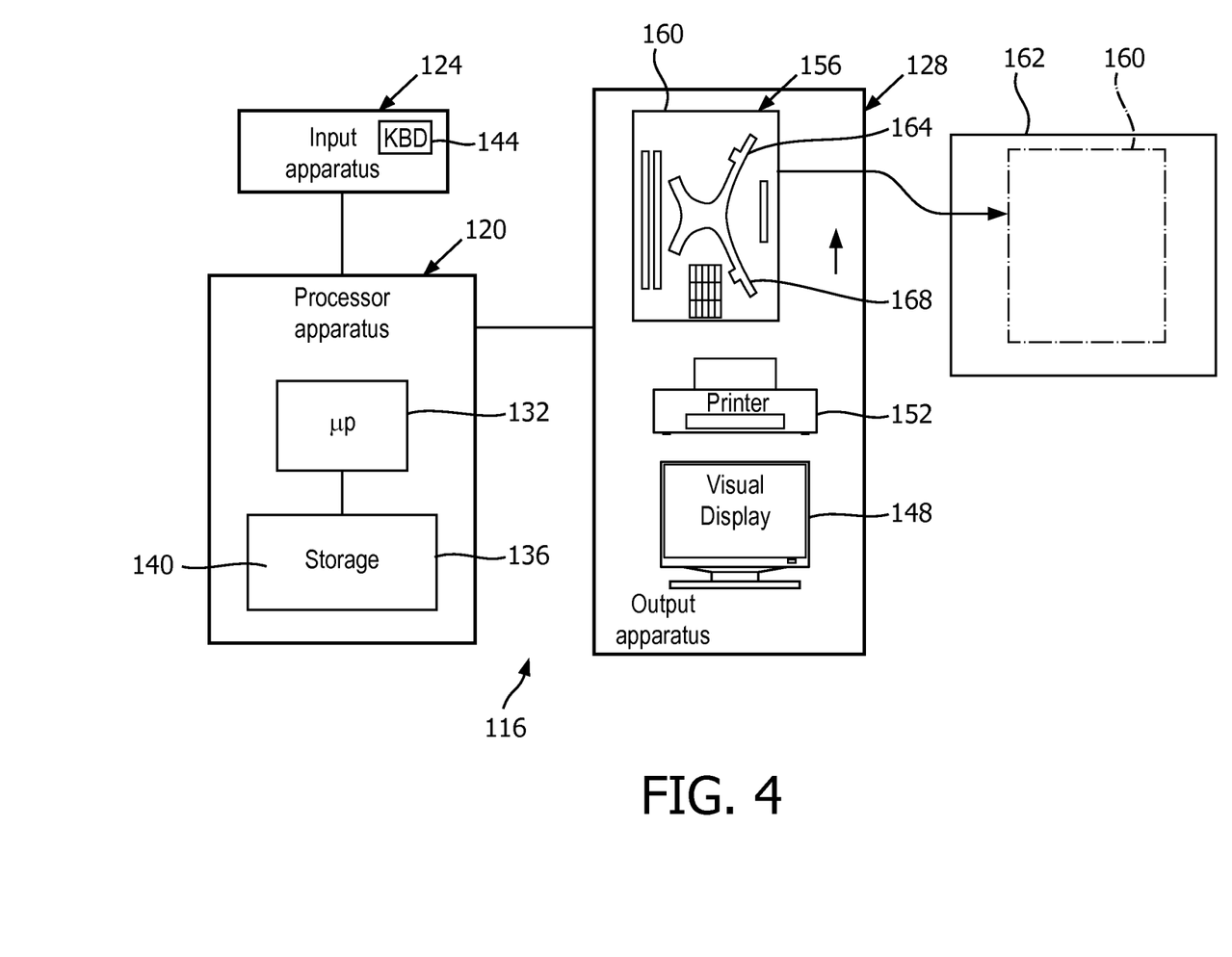
FIG. 4 is a schematic depiction of a computer upon which the method is, at least in part, performed.

Input apparatus 124 can be said to include a keyboard 144 and any of a variety of other input devices such as a mouse, a touchpad, a barcode reader, and the like, without limitation. Output apparatus 128 is depicted in FIG. 4 as including a visual display 148 and a printer 152 among other output devices.

In general terms, the aforementioned parameters are uploaded to computer 116 via input apparatus 124 or otherwise, and the parameters are then subjected to one or more algorithms that are embodied in routines 140 being executed by processor 132. Such subjecting of the parameters to the various algorithms, tables, or other techniques or combination of techniques enables computer 116 to determine various lengths of physical features 20, various angles between physical features 20, and other properties and values, which together generate a configuration for headgear 4. That is to say, the various lengths of physical features 20, i.e., of the straps of strap apparatus 28, and the angles between various physical features 20, i.e., between the straps of strap apparatus 28, together with other properties and values, together define the configuration of headgear 4 that is generated by the algorithms based at least in part upon the various parameters that pertain to head 84 and that are subjected to the algorithms.

Routines 140 can be said to together form a model that is used to generate the configuration of headgear 4 in response to the various parameters that are received from patient 16. The model also generates from the configuration a pattern 156 that is imprinted onto a sheet of paper 160 (FIGS. 7 and 8) or other substrate by printer 152. By way of example, the sheet of paper 160 that includes pattern 156 can then be overlaid on a sheet of material 162 such as cloth or other appropriate material in order to enable the various components from which headgear 4 will be formed to be cut from sheet of material 162, such as by using scissors or the like, and by following pattern 156. Sheet of material 162 in the depicted exemplary embodiment is a sheet of fabric that is of in appropriate configuration and density for formation of headgear 4. Furthermore, additional or other sheets of material can be employed to form various parts of headgear 4 without departing from the spirit of the present concept.

Figure 5:
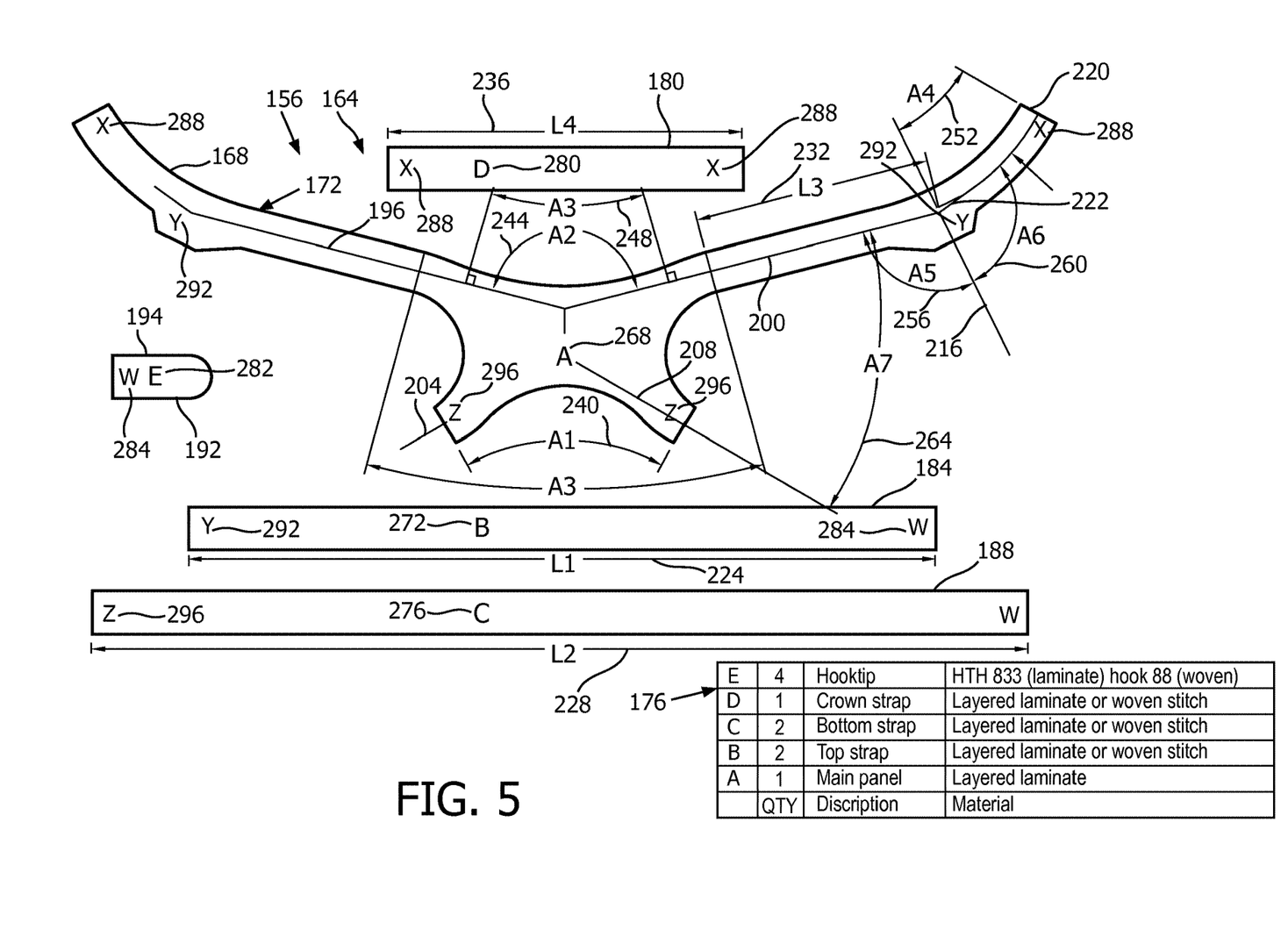
FIG. 5 is an exemplary depiction of the various components that form a pattern that is output from the computer in accordance with the method of the present invention.
Figure 7:
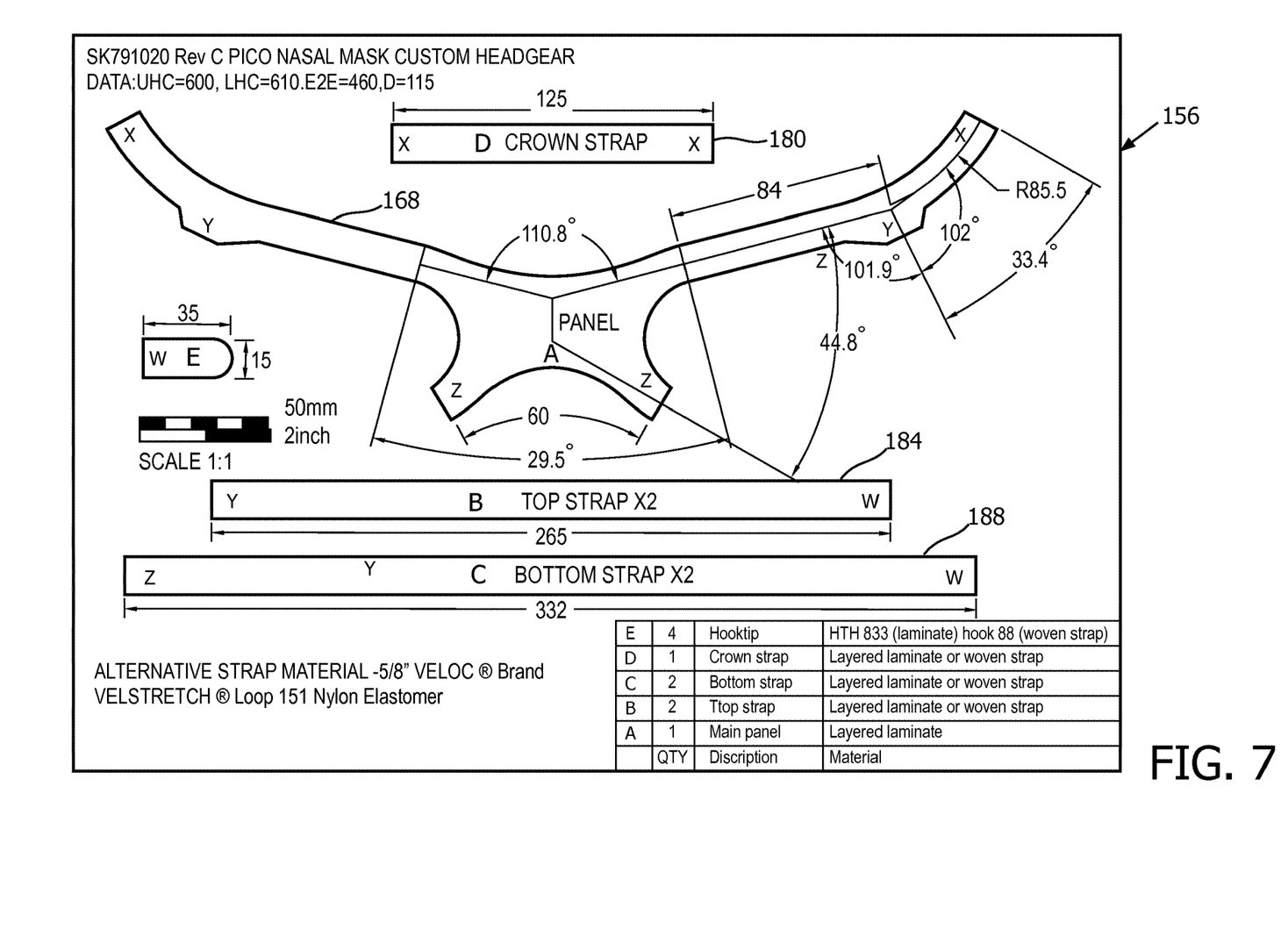
FIG. 7 is an exemplary depiction of a pattern that is output and that includes the components shown in FIG. 5.
Figure 8:
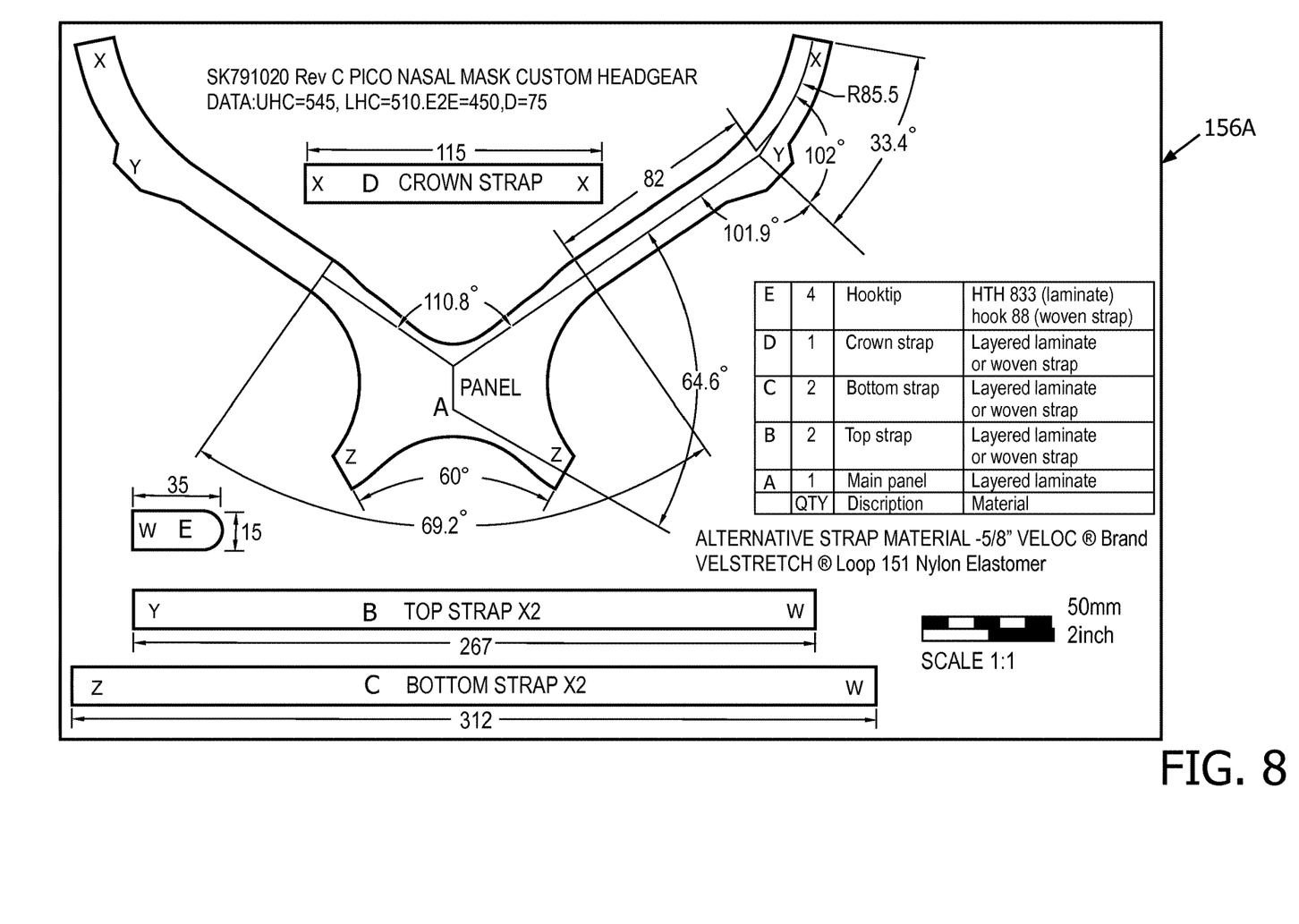
FIG. 8 is an exemplary depiction of another pattern that is output from the computer in accordance with the improved method in response to different input parameters being received.

FIG. 5 depicts certain elements which, when visually output, will form a pattern 156 such as is shown in FIGS. 7 and 8. Pattern 156 includes an amount of imprinted content 164, much of which is depicted in FIG. 5, and which, in the depicted exemplary embodiment, includes a first outline 168 that is an outline of a body 172 of headgear 4. In the depicted exemplary embodiment, the model that generates the configuration of headgear 4 from the aforementioned parameters also configures body 172 to include base 24, left and right occipital straps 44 and 56, and left and right chin attachment points 72 and 80. By employing first outline 168 to cut from sheet of material 162 body 172, the resulting body 172 that is formed therefrom will include the aforementioned physical features 20 (base 24, left and right occipital straps 44 and 56, and left and right chin attachment points 72 and 80) of headgear 4 as a single piece unitary structure. It is understood that in other embodiments the model could create as body 172 another combination of physical features 20 individually or in any combination that is suitable. As such, it is understood that the exemplary first outline 168 is merely one fashion in which at least a portion of the various components or physical features 20 of headgear 4 can be arranged according to the aforementioned configuration of headgear for that is generated by computer 116, and it is thus understood that variations can be employed without departing from the spirit of the instant disclosure.

As can be understood from FIG. 5, the exemplary imprinted content 164 further includes a bill of materials 176 that expressly identifies the other parts and, if applicable, the quantity thereof that should be made, in order to enable headgear 4 to be assembled from such components and from body 172. The imprinted content 164 additional includes a second outline 180 that is an outline of parietal strap 32, a third outline 184 that is an outline of left and right temporal straps 36 and 40, and a fourth outline 188 that is an outline of left and right chin straps 68 and 76. In this regard, it is understood that left and right temporal straps 36 and 40 are mirror images of one another and that left and right chin straps 68 and 76 are likewise mirror images of one another in the depicted exemplary embodiment. Depending upon the needs of the particular application, separate outlines for such straps can be provided rather than simply providing a single outline that is employed for forming a pair of straps therefrom. This might be useful in a scenario where, for instance, left and right temporal straps 36 and 40 might not be mirror images of one another, and/or wherein left and right chin straps 68 and 76 are not mirror images of one another.

The exemplary imprinted content 164 further includes a fifth outline 192 that is employed in conjunction with a sheet of hook material to generate a plurality of hook attachments 194 that are usable at some of the ends of the straps of strap apparatus 28. That is, hook attachments 194 are affixed to some of the ends of the straps of strap apparatus 28, and hook attachments 194 thereby each enable such an end of a strap to be turned back on itself to enable the hooks of hook attachment 194 to be engaged with corresponding loops that are formed on the corresponding strap, This enables the formation of hook-and-loop attachments or fasteners that enable such straps to be connected with mask component 8.

As a general matter, once pattern 156 has been output by printer 152, the various components that are specified by pattern 156 can be formed out of sheet of material 162 and other sheets of material, as appropriate, in order to form the various components that are specified in bill of materials 176. The various components can then be assembled together to form headgear 4. Such assembly may involve sewing together of certain of the various components with one another in a fashion that will be set forth in greater detail below.

Figure 3:
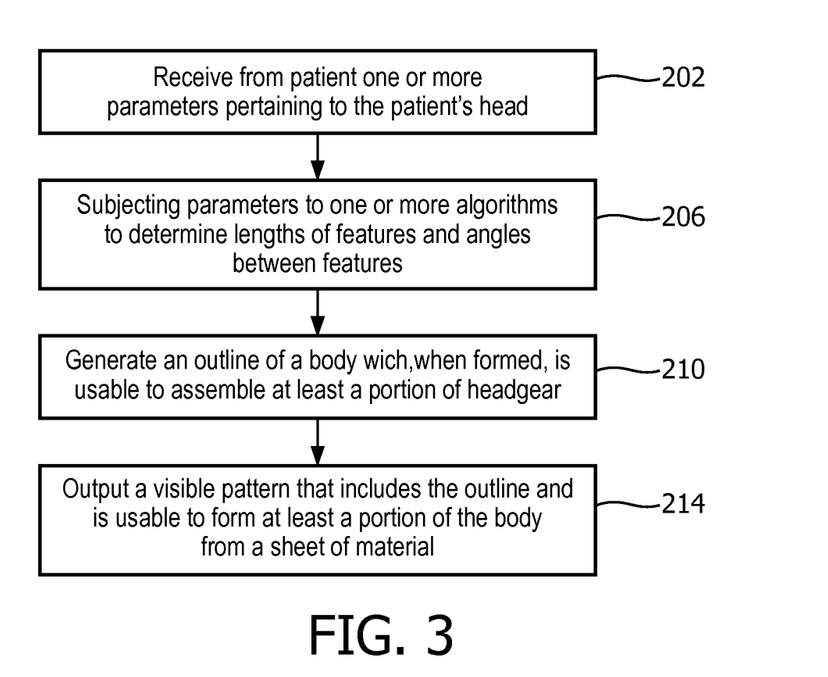
FIG. 3 is a flowchart depiction certain aspects of the method of the present invention.

FIG. 3 depicts an exemplary flowchart that describes in general terms how pattern 156 is developed by routines 140 from the aforementioned parameters that pertain to head 84 and that are received from patient 16. Specifically, and as at 202, computer 116 receives from patient 16 one or more of the parameters that pertain to head 84 of patient 16. The parameters are then subjected, as at 206, to one or more algorithms tables, or other techniques or combination of techniques that are embodied in routines 140 and the model in order to determine various lengths of physical features 20 and angles between physical features 20, and the like. Routines 140 then generate, as at 210, one or more outlines, such as any one or more of first outline 168, second outline 180, third outline 184, fourth outline 188, and fifth outline 192. Such outlines, when formed from sheet of material 162 and/or other sheets of material or other materials, are usable to assemble at least a portion of headgear 4 according to the configuration that has been generated by routines 140.

Computer 116 then outputs, as at 214, pattern 156 in a visible form that includes bill of materials 176 and one or more of the aforementioned outlines such as first outline 168, second outline 180 third outline 184, fourth outline 188, and fifth outline 192. Such outlines enable body 172 and other of the physical features 20 to be formed from sheet of material 162 and other sheets of material, as appropriate.

As can be understood from FIG. 5, left occipital strap 44 is elongated and can be said to have an axis of elongation 196, and right occipital strap 56 can likewise be said to be elongated and to have an axis of elongation 200. Left chin strap 68 similarly is elongated and has an axis of elongation 204 that is depicted as extending from left chin attachment point 72, and right chin strap 76 likewise is elongated and has an axis of elongation 208 that is depicted as extending from right chin attachment point 80. In a likewise fashion, left temporal strap 36 is elongated and has an axis of elongation 202 that is depicted as extending from left temporal attachment point 48, and right temporal strap 40 is similarly elongated and has an axis of elongation 216 that is depicted as extending from right chin attachment point 60. Furthermore, parietal strap 32, as will be set forth in greater detail below, is ultimately going to be affixed to the ends of left and right parietal attachment points 52 and 64. While left and right parietal attachment points 52 and 64 are themselves curved, an end 220 of right parietal attachment point 62 is situated in a particular orientation with respect to axis of elongation 216, and left parietal attachment point 52 is a mirror image thereof.

As can further be seen from FIG. 5, left and right temporal straps 36 and 40 are of an exemplary equal temporal length (L1) 224, and left and right chin straps 68 and 76 are of an exemplary equal chin length (L2) 228. In a similar fashion, left and right occipital straps 44 and 56 are of an exemplary equal occipital length (L3) 232, and parietal strap 32 is of a parietal length (L4) 236. While lengths L1, L2, L3, and L4, which are indicated at numerals 224, 228, 232, and 236, respectively, are depicted in FIG. 5, such lengths need not necessarily be expressly output as part of imprinted content 164 of pattern 156, and rather it is anticipated that such express lengths typically would be absent from pattern 156.

FIG. 5 further depicts an angle A1 240 as being the angle between the free ends of left and right chin attachment points 72 and 80. An angle A2 244 is depicted in FIG. 5 as being the angle between axis of elongation 196 and axis of elongation 200. An angle A3 248 is the angle between perpendiculars from axis of elongation 196 and axis of elongation 200, whereby A3+A2=180 degrees. Another angle A4 252 is an angle between end 220 of right parietal attachment point 64 and direction of elongation 216 of right temporal strap 40, which is equal to another angle A4 at the opposite side of body 172 that is not expressly depicted herein for reasons of simplicity. Another angle A5 256 is the angle between the aforementioned direction of elongation 216 of right temporal strap 40 and axis of elongation 200. Another angle A6 260 is the angle between the aforementioned direction of elongation 216 of right temporal strap 40 and an axis of elongation 222 of right parietal attachment point 64 at it extends from right temporal attachment point 60. An additional angle A7 264 is the angle between axis of elongation 200 and axis of elongation 208.

Figure 6:
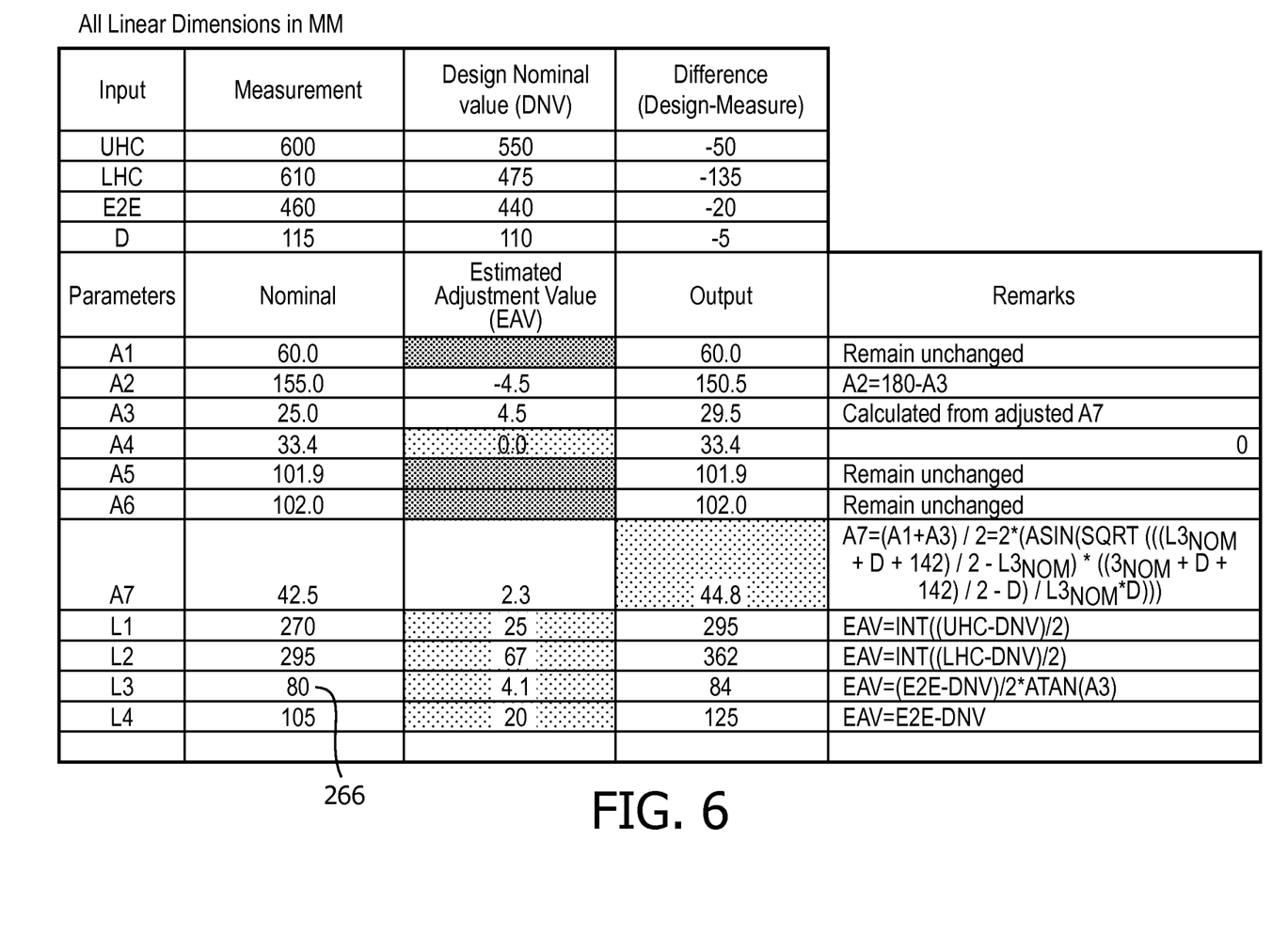
FIG. 6 is a chart depicting exemplary relationships among various parameters used in creating the pattern.

The interrelationships between the various aforementioned lengths and the various aforementioned angles of the various physical features 20 are set forth in FIG. 6. The model is configured to begin with a nominal value for each of the aforementioned angles and lengths, as is indicated under the heading "Nominal" in FIG. 6. The model is further configured to employ the aforementioned parameters that pertain to head 84, i.e., UHC 88, LHC 96, E2E 108, and D 112, to calculate an Estimated Adjustment Value (EAV) that is applied to the nominal valued in order to adjust the nominal values, as appropriate, to generate corresponding output values, as is indicated under the heading "Output" in FIG. 6. The Output heading of FIG. 6 lists the various adjusted values of lengths L1, L2, L3, and L4 and angles A1 through A7, i.e., the values that result when the nominal values are adjusted by the EAV values, and that are embodied by the model into the configuration of headgear 4 from which the model generates pattern 156. In the depicted exemplary embodiment, A1 240, A4 252, A5 256, and A6 260 remain unchanged, although in other embodiments in accordance with the disclosed and claimed concept, they potentially can change depending upon the received parameters and/or depending upon how the model is designed. The lengths L1 224, L2 228, L3 232, and L4 236 are calculated based upon the received parameters UHC 88, LHC 96, E2E 108, and D 112 all as indicated in the "Remarks" portion of FIG. 6. FIG. 6 thus can be said to depict certain of the algorithms to which the parameters are subjected.

An additional algorithm that is set forth below is employed to calculate A7 264 based upon the nominal value of L3, which is indicated as $L3_{NOM}$ at the numeral 266 in FIG. 6, and the length D 112 received as a parameter that pertains to head 84. The algorithm is as follows: $A7=2*(ASIN(SQRT(((L3_{NOM}+D+142)/2-L_{NOM})*((L3_{NOM}+D+142)/2-D)/L3_{NOM}*D)))$.

As can further be seen from FIG. 6, L1 224, L2 228, L3 232, and L4 236 are calculated based upon the measured and received parameters UHC 88, LHC 96, and E2E 108 and a corresponding Design Nominal Value (DNV) of the parameter. By way of example, therefore, and in case of L1 224, the Estimated Adjustment Value (EAV) equals INT (UHC−DNV)/2. In the given example, the measurement of UHC received from patient 16 is 600 mm, and the corresponding DNV of UHC is 550 mm. As such the EAV for UHC=INT ((600−550)/2), which is equal to 25 mm. The nominal value for L1 is 270 mm, so when EAV of 25 mm is added thereto, the output for L1 is 295 mm, and third outline 184 will be drawn as part of pattern 156 to reflect this dimension, meaning that third outline 184 will be drawn as a rectangle having a length of 295 mm. All dimensions are expressed in terms of millimeters, although other measurement schemes such as inches and the like can be employed without departing from the present concept.

Based upon all of the aforementioned algorithms, the various values for lengths L1-L4 and angles A1-A7 are calculated, and routines 140 calculate first outline 168 of body 172 and second, third, and fourth outlines 180, 184, and 188. Fifth outline 192 is fixed in the depicted exemplary embodiment and it is based upon the known strength and attachment characteristics of the hook and loop fasteners that result from use of hook attachments 194.

The various outlines and bill of materials 176 are then generated as imprinted content 164 that is imprinted as pattern 156 on sheet of paper 160, such as is shown in FIG. 7, as an output from printer 152. Pattern 156 typically will not include the express indications of lengths L1-L4 or angles A1-A7 such as are shown in FIG. 5 for purposes of disclosure. Rather, pattern 156 typically will include the aforementioned outlines, perhaps some dimensions, and the indicia that is mentioned below. By way of further example, FIG. 8 depicts an alternative pattern 156A whose various lengths and angles are different from those of pattern 156 based upon different parameters being input. As mentioned, pattern 156 is then employable atop sheet of material 162 and other sheets of material in order to form the various components from which headgear 4 is formed.

More specifically, various of the components are sewn to one another in order to form headgear 4. In order to facilitate such sewing or other method of affixation, various indicia are included as a part of imprinted content 164 and which facilitates the person making the various components of headgear 4 from pattern 156 to visualize and assemble such components together. For instance, for example, an indicium "A" 268 is imprinted on first outline 168 and is also indicated in bill of materials 176 as corresponding with "main panel" which refers to body 172. Likewise, an indicium "B" 272 is applied to third outline 184 and is indicated in bill of materials 176 as corresponding with "top strap" which refers to left and right temporal straps 36 and 40. In a similar fashion, an indicium "C" 276 is imprinted on sheet of paper 160 within fourth outline 188 and can be seen in bill of materials 176 as corresponding with "bottom strap" which refers to left and right chin straps 68 and 76. Likewise, an indicium "B" 280 is imprinted on second outline 180 and can be seen in bill of materials 176 as corresponding with "crown strap" which refers to parietal strap 32. In a like fashion, indicium "E" 282 is printed within fifth outline 192 and can be seen in bill of materials 176 as referring to "hook tip" which refers to hook attachments 194. Bill of materials 176 thus identifies the significance of the various outlines thereon and also provides in the "QTY" column the quantity of each that is to be formed from each such outline.

Advantageously, pattern 156 includes other indicia that facilitate assembly of headgear 4 from the various components that are generated from pattern 156. For example, indicium "W" 284 is imprinted at the rightmost end of each of third and fourth outlines 184 and 188, and is also imprinted within fifth outline 192. This suggests that hook attachments 194, that are formed from fifth outline 192, are to be affixed to the rightmost (from the perspective of FIG. 5) end of each of the straps that are cut from sheet of material 162 using third and fourth outlines 184 and 188 and that will be used to form left and right temporal straps 36 and 40 and left and right chin straps 68 and 76.

Additionally, another indicium "X" 288 is applied at the opposite ends of second outline 180 and also at the free ends of left and right parietal attachment points 52 and 64, which suggests that the ends of parietal strap 32 should be affixed to free ends of left and right parietal attachment points 52 and 64. Another indicium "Y" 292 is depicted in FIG. 5 as being imprinted at the left end (from the perspective of FIG. 5) of third outline 184 and also on left and right temporal attachment points 48 and 60, which suggests that an end of left temporal strip 36 should be affixed to left temporal attachment point 48 and that an end of right temporal strap 40 should be affixed to right temporal attachment point 60. A still further indicium "V" 296 is depicted as being printed at the leftmost (from the perspective of FIG. 5) end of fourth outline 188 and also on left and right chin attachment points 72 and 80, which would suggest that the end of left chin strap 68 should be affixed to left chin attachment point 72 and that the end of right chin strip 76 should be affixed to right chin attachment point 80. While the aforementioned attachments between the various straps and body 172 are envisioned to occur via sewing, any appropriate attachment methodology may be employed without departing from the spirit of the present disclosure.

Once the various components are affixed to body 172, as set forth above, headgear 4 is fully formed and can be attached to mask component 8. This would involve receiving certain of the straps through appropriate openings formed in mask component 8 and turning the ends of such straps back upon themselves to enable hook attachments 194 to engage loop portions on headgear 4 to create detachable connections. Other attachment methodologies between headgear 4 and mask component 8 can be envisioned.

It is noted that the advantageous method may additionally give to patient 16 the option to choose where pattern 156 is output, such as at a location where printer 152 and sheet of material 162 are situated, and where technicians or other workers are present and can cut the various components from sheet of material 162 and can form headgear 4 therefrom. For instance, retailers such as Jo-Ann Fabric and Craft Stores, Michaels Craft Stores, Pat Catan's Arts and Crafts Stores, and the like may form a business relationship with a medical insurer or with the developer of the model that is used to create headgear 4. Patient 16 may be given an opportunity to choose, and patient may therefore choose, which of these plurality of locations and other locations will be the location where headgear 4 is manufactured. Offering choice to patient 16 promotes satisfaction with the final resultant headgear 4 and permits patient to participate in the decision making process regarding his or her healthcare, which is desirable. Moreover, multiple models may exist, and patient may be afforded the opportunity to choose a model from among several competing models will be used to create headgear 4, and the resultant headgear can be manufactured at any of the aforementioned plurality of locations. Other options can be envisioned. For instance, patient 16 can print the pattern himself or herself and can manually build headgear 4. Additionally or alternatively, patient 16 can choose the fabrics, colors, textures, etc. of the sheet of material 162.

It thus can be seen that the improved method enables a variety of parameters that are received from patient to be employed to create a configuration of headgear 4 which is output as a pattern 156 that is usable to generate from sheet of material 162 various components that are assembled together to form headgear 4. Since headgear 4 is customized to be particular dimensions of head 84 of patient 16, fit is improved and comfort is thus likewise correspondingly improved. Other advantages will be apparent.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of generating a configuration for a headgear that is customized for a particular patient who is in need of respiratory therapy, the headgear having a plurality of physical features and being usable with a mask component that supplies a flow of breathing gas to the patient's airways, the method comprising:

receiving one or more parameters pertaining to the patient's head;

subjecting at least some of the parameters to one or more algorithms to determine at least one of a length of a physical feature of the plurality of physical features and an angle between a pair of physical features of the plurality of physical features;

generating an outline of at least a portion of a body which, when formed, is usable to assemble therefrom at least a portion of the headgear, the outline including the at least one of a length of a physical feature of the plurality of physical features and an angle between a pair of physical features of the plurality of physical features;

outputting a pattern that is visible and that comprises the outline, the pattern being usable to enable the formation of the at least a portion of the body from at least a first sheet of at least a first material;

configuring at least a portion of the body to comprise at least some of the physical features of the plurality of physical features and at least one of the one or more attachment points that are each structured to have a strap attached thereto and one or more straps;

outputting as at least a portion of the pattern the at least some of the physical features configuring the pattern to include at least a first strap perimeter that is separate from the outline and that is usable to enable the formation, separate from the body, of at least a first strap from a sheet of material, the at least first strap being structured to be attached to an attachment point from among the one or more attachment points outputting the pattern by imprinting it onto a substrate imprinting on the pattern in the vicinity of an end of the at least first strap perimeter an instance of an indicium; and imprinting on the pattern in the vicinity of a portion of the outline that corresponds with the attachment point another instance of the indicium; and configuring at least a portion of the body to comprise a base and to further comprise as the at least some of the physical features:
- a plurality of straps extending away from the base, a pair of straps of the plurality of straps each having an axis of elongation;
- a plurality of attachment points that are each structured to have a strap attached thereto, a pair of attachment points of the plurality of attachment points each protruding from the base along a direction of protrusion, and
- the axis of elongation of a strap of the pair of straps and a direction of protrusion of an attachment point of the pair of attachment points being oriented at the angle with respect to one another.

2. The method of claim 1, further comprising outputting a proposed bill of materials.

3. The method of claim 1, further comprising receiving from the patient the one or more parameters.

4. The method of claim 1, further comprising further configuring the at least some of the physical features such that the axes of elongation of the pair of straps are oriented at another angle with respect to one another, the another angle being based at least in part upon at least a portion of the one or more parameters.

5. The method of claim 1, further comprising further configuring the at least some of the physical features such that the pair of straps are each of the length.

6. The method of claim 5, further comprising additionally configuring the at least some of the physical features such that the another pair of attachment points of the plurality of attachment points are situated on the pair of straps at a distance from the base equal to the length.

7. The method of claim 6, further comprising also configuring the at least some of the physical features such that the at least first strap is another pair of straps that are each of a predetermined length based at least in part upon at least a portion of the one or more parameters, each strap of the another pair of straps being structured to be attached to a corresponding attachment point of the another pair of attachment points.

8. The method of claim 6, further comprising furthermore configuring the at least some of the physical features such that they further comprise a pair of attachment devices that are structured to be attached to the another pair of straps at the free ends thereof opposite the another pair of attachment points, each attachment device of the pair of attachment devices enabling the free end of a corresponding strap of the another pair of straps on which the attachment device is situated to be turned back on itself and attached to the corresponding strap at a location along its midsection.

9. The method of claim 1, further comprising offering to the patient an option to choose a location from among a plurality of locations at which the pattern will be output and assembled.

* * * * *